United States Patent
Kato et al.

(10) Patent No.: US 9,725,307 B2
(45) Date of Patent: Aug. 8, 2017

(54) METHOD FOR PRODUCING MICROCHANNEL, AND MICROCHANNEL

(71) Applicants: CITIZEN WATCH CO., LTD., Tokyo (JP); KEIO UNIVERSITY, Tokyo (JP)

(72) Inventors: Seiko Kato, Saitama (JP); Masafumi Ide, Saitama (JP); Takaaki Nozaki, Saitama (JP); Takaaki Takeishi, Saitama (JP); Takaaki Ishigure, Kanagawa (JP); Kazutomo Soma, Kanagawa (JP)

(73) Assignees: CITIZEN WATCH CO., LTD., Tokyo (JP); KEIO UNIVERSITY, Tokyo (JP)

( * ) Notice: Subject to any disclaimer, the term of this patent is extended or adjusted under 35 U.S.C. 154(b) by 74 days.

(21) Appl. No.: 14/655,239

(22) PCT Filed: Dec. 18, 2013

(86) PCT No.: PCT/JP2013/083951
§ 371 (c)(1),
(2) Date: Jun. 24, 2015

(87) PCT Pub. No.: WO2014/103842
PCT Pub. Date: Jul. 3, 2014

(65) Prior Publication Data
US 2015/0329354 A1    Nov. 19, 2015

(30) Foreign Application Priority Data
Dec. 28, 2012   (JP) .................................. 2012-288628

(51) Int. Cl.
*B81C 1/00*    (2006.01)
*B01J 19/00*    (2006.01)
(Continued)

(52) U.S. Cl.
CPC ....... *B81C 1/00071* (2013.01); *B01J 19/0093* (2013.01); *B01L 3/502707* (2013.01);
(Continued)

(58) Field of Classification Search
CPC .... B81C 1/00071; B81C 1/00; B01J 19/0093; B01J 2219/00783; B01J 2219/00883;
(Continued)

(56) References Cited

U.S. PATENT DOCUMENTS 7,585,462 B2 *   9/2009   Parng ................ B01L 3/502746
                                                        422/417

FOREIGN PATENT DOCUMENTS

JP          2003-311697 A       11/2003
JP          2003311697 A    *   11/2003
(Continued)

OTHER PUBLICATIONS

Written Opinion of the International Searching Authority for PCT/JP2013/083951, Mar. 18, 2014.
(Continued)

*Primary Examiner* — James M Mellott

(57) ABSTRACT

Provided is a method for producing a microchannel including an approximately circular cross section with neither a joined surface nor an inlet in a smaller number of steps than has been conventional. The method for producing a microchannel includes the steps of forming a layer of an uncured curable resin (2) on a substrate (1), inserting into the curable resin a needle body (3) that can inject a liquid (4), injecting a liquid in a tubular shape into the curable resin via the needle body while moving the needle body, extracting the needle body from the curable resin, and curing the curable resin to form a channel (4A) in a tubular region injected with the liquid.

4 Claims, 4 Drawing Sheets

(51) Int. Cl.
- *B01L 3/00* (2006.01)
- *B29C 67/00* (2017.01)
- *B29C 35/08* (2006.01)
- *B81B 1/00* (2006.01)
- *C12M 3/06* (2006.01)
- *G01N 37/00* (2006.01)

(52) U.S. Cl.
CPC ............ *B29C 67/0048* (2013.01); *B81B 1/00* (2013.01); *B81C 1/00* (2013.01); *C12M 23/16* (2013.01); *G01N 37/00* (2013.01); *B01J 2219/0086* (2013.01); *B01J 2219/00783* (2013.01); *B01J 2219/00833* (2013.01); *B01L 2300/12* (2013.01); *B29C 2035/0827* (2013.01); *B81B 2203/0338* (2013.01); *Y10T 428/24744* (2015.01)

(58) Field of Classification Search
CPC ........ B01J 2219/0086; B01L 3/502707; B01L 2300/12; B29C 67/0048; B29C 2035/0827; C12M 23/16; G01N 37/00; Y10T 428/24744

See application file for complete search history.

(56) References Cited

FOREIGN PATENT DOCUMENTS

| | | | |
|---|---|---|---|
| JP | 2007-216086 A | | 8/2007 |
| JP | 2007216086 A | * | 8/2007 |
| JP | 2012-137325 A | | 7/2012 |
| JP | WO 2013002013 A1 | * | 1/2013 ........... G02B 6/1221 |
| WO | 2013/002013 A1 | | 1/2013 |

OTHER PUBLICATIONS

International Search Report for PCT/JP2013/083951, Mar. 18, 2014.

Teruo Fujii Laboratory, "Fabrication of semi-round microchannels using a fluid dispenser and its application to a flow regulator", Tokyo University, 2011 http://www.microfluidics.iis.u-tokyo.ac.jp/r11016_j.html.

Rui Lima et al., "Axisymmetric PDMS microchannels for in vitro haemodynamic studies", Biofabrication, Sep. 2009, vol. 1.

Jeffery T. Borenstein et al., "Functional endothelialized microvascular networks with circular crosssections in a tissue culture substrate", Biomed Microdevices, Feb. 2010, vol. 12, pp. 71-79.

* cited by examiner

FIG. 1
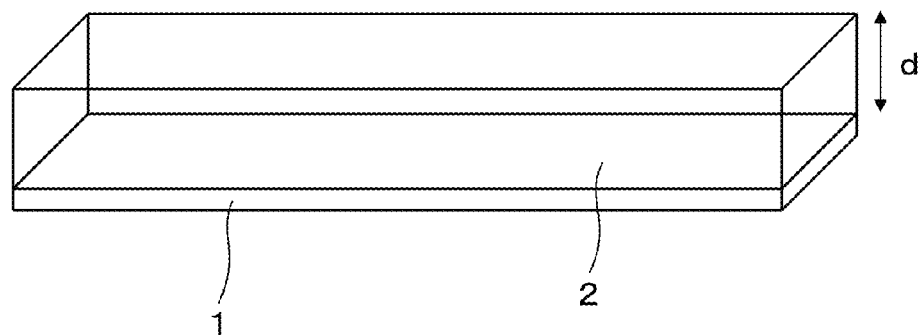
(A)
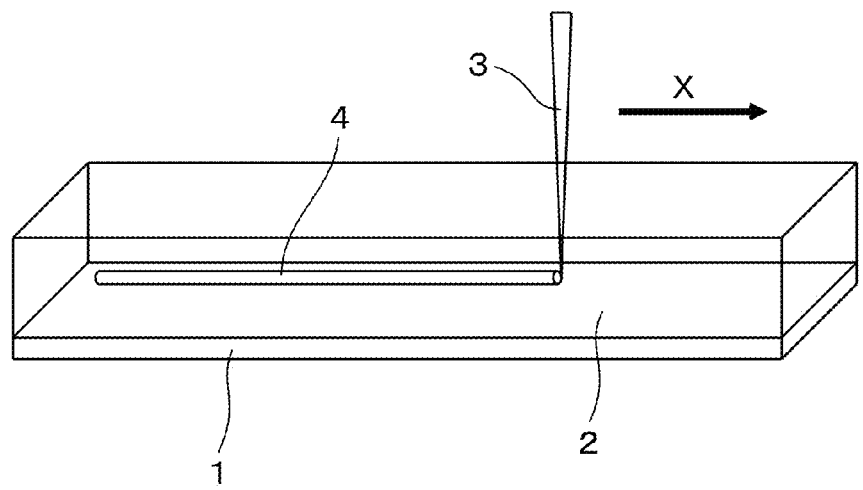
(B)
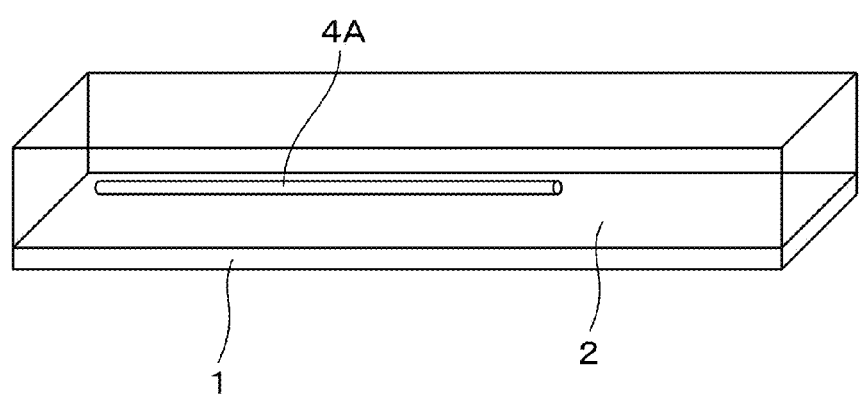
(C)

FIG. 3
(A)
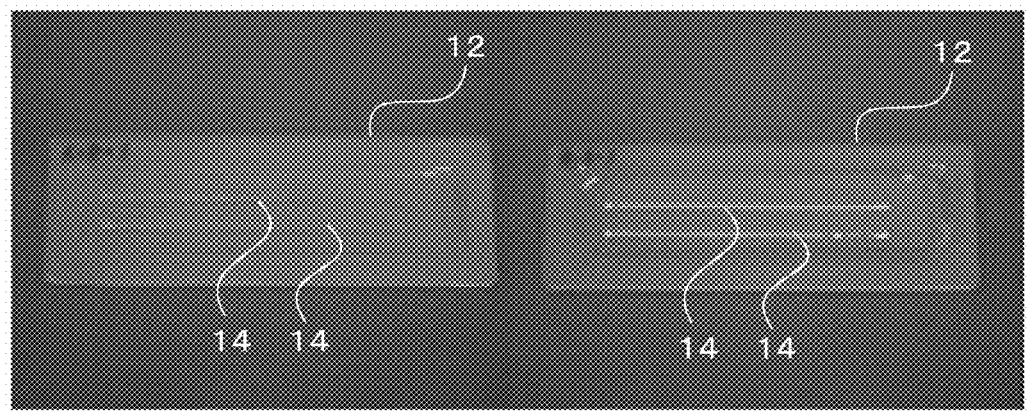
(B)
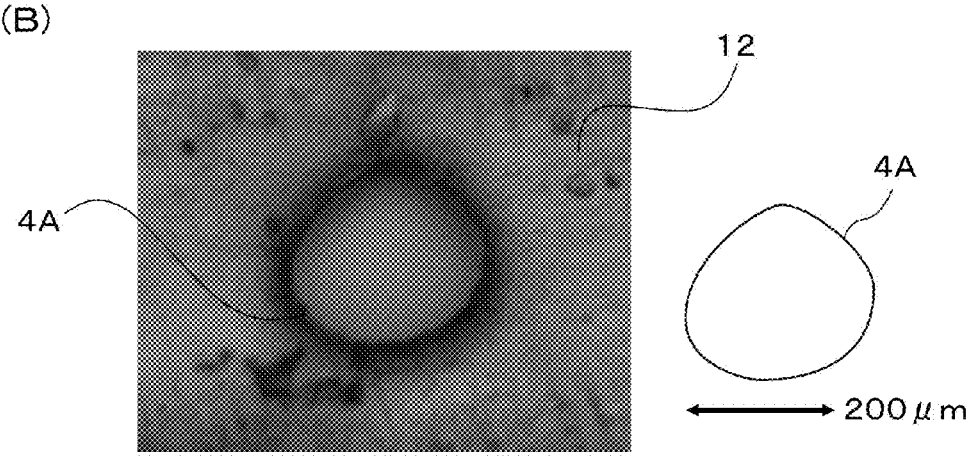

US 9,725,307 B2

METHOD FOR PRODUCING MICROCHANNEL, AND MICROCHANNEL

TECHNICAL FIELD

The present invention relates to a method for producing a microchannel, and to a microchannel.

BACKGROUND

Microfluidic devices in which liquids and the like are allowed to flow through microchannels having diameters of around several μm to several-hundred μm to effect biochemical reactions, to perform physicochemical separation manipulations, and the like have been known. In such a microfluidic device, a channel having a semicircular or circular cross section is needed. However, since a channel having a rectangular cross section has been often produced in a photolithography step widely used for producing a microfluidic device, a method for producing a channel having a semicircular or circular cross section has been proposed.

Patent Literature 1 describes a method for producing a microchannel device including a pair of half-divided bodies that have long plate shapes and include a groove formed on one face thereof and opened in a semicircular shape in one-end face, in which the half-divided bodies are joined.

Non Patent Literature 1 describes a method for producing a channel having a circular cross section. In this method, using a dispenser robot for automatically applying an adhesive or the like used when electronic equipment is produced, an ultraviolet-curable resin or the like is directly drawn in a channel pattern shape on a substrate to produce a mold. Then, channels having semicircular cross sections are produced by performing molding with PDMS (polydimethylsiloxane) using the produced mold. In addition, a channel for a circular cross section is produced by affixing the channels with semicircular cross sections to each other.

Non Patent Literature 2 describes a method for producing a circular PDMS microchannel which is suitable for visualization of micro-flow and simulates microvessels in vivo, such as confocus μPIV/PTV (Particle Image Velocimetry/Particle Tracking Velocimetry). In this method, a circular channel is formed by curing PDMS in a state in which a wire is embedded and then pulling the wire out.

Non Patent Literature 3 describes a method for configuring a microvascular network having a circular cross section from a polystyrene sheet. In this method, a semicircular master with silicon is configured in an electroplating step and embossed on polystyrene sheets, and the two obtained sheets are joined to form a channel having a circular cross section.

CITATION LIST

Patent Literature

Patent Literature 1: Japanese Laid-open Patent Publication No. 2012-137325

Non Patent Literature

Non Patent Literature 1: "Fabrication of semi-round microchannels using a fluid dispenser and its application to a flow regulator", Teruo Fujii Laboratory, Tokyo University, [online], [searched on Dec. 17, 2012], the Internet<URL: http://www.microfluidics.iis.u-tokyo.ac.jp/r11016_j.html>

Non Patent Literature 2: Rui Lima et al., "Axisymmetric PDMS microchannels for in vitro haemodynamic studies", Biofbrication, 2009, vol. 1

Non Patent Literature 3: Jeffery T. Borenstain et al., "Functional endothelialized microvascular networks with circular cross-sections in a tissue culture substrate", Biomed Microdevices, 2010, vol. 12, p. 71-79

SUMMARY

However, a production method, in which plural channels with semicircular cross sections are formed and the channels are affixed to each other, includes a number of steps and is complicated. Additionally, since cavities are affixed to each other, it is difficult to form a channel while maintaining a circular shape.

In the method of Non Patent Literature 2, a circular channel is formed without affixing channels with semicircular cross sections to each other; however, since the method includes the step of pulling the wire out, it is impossible to form a channel without any inlet but it is possible to form only a channel with a simple structure with a straight line shape or the like. Additionally, in the method of Non Patent Literature 2, a step of injecting a liquid into the formed channel is needed for obtaining the channel into which the liquid is injected.

Thus, an objective of the present invention is to provide a method for producing a microchannel including an approximately circular cross section with neither a joined surface nor an inlet in a smaller number of steps than has been conventional.

Provided is a method for producing a microchannel including the steps of forming a layer of an uncured curable resin on a substrate, inserting into the curable resin a needle body that can inject a liquid, injecting a liquid in a tubular shape into the curable resin via the needle body while moving the needle body, extracting the needle body from the curable resin, and curing the curable resin to form a channel in a tubular region injected with the liquid.

Preferably, in the above method, the channel is a channel comprising an approximately circular cross section without any joined surfaces.

Preferably, the above method further includes the step of removing a part of the cured curable resin to extract the liquid confined within the curable resin.

Preferably, in the above method, the liquid is a liquid crystal.

Additionally, a microchannel produced by any one of the above methods is provided.

The present invention makes it possible to produce a microchannel including an approximately circular cross section with neither a joined surface nor an inlet in a smaller number of steps than has been conventional.

BRIEF DESCRIPTION OF THE DRAWINGS

FIG. 1(A) to (C) are schematic views for explaining a method for producing a microchannel;

FIGS. 3(A) and (B) are photographs representing the experimental results of the production method of FIG. 2.

DESCRIPTION

Hereinafter, with reference to the drawings, a method for producing a microchannel will be explained in detail. However, it should be noted that the technical scope of the present invention is not limited to embodiments thereof and includes the invention described in claims and equivalents thereof.

Figure 2:
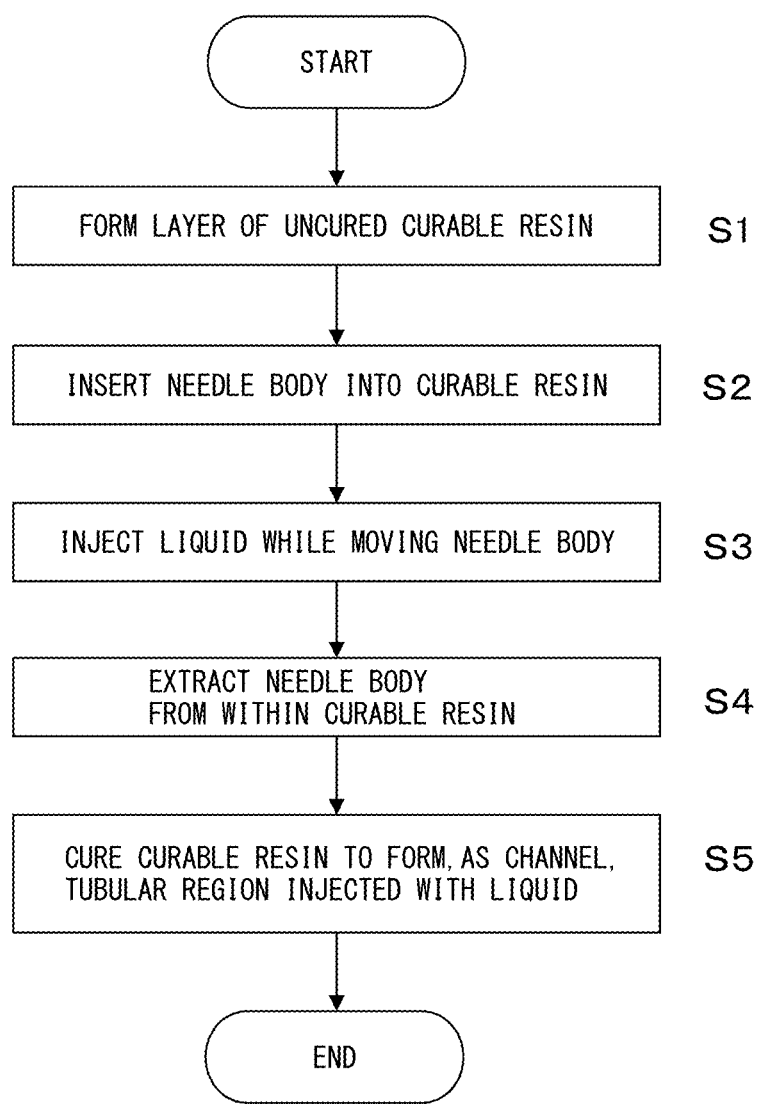
FIG. 2 is a flowchart representing the method for producing a microchannel.

FIG. 1(A) to FIG. 1(C) are schematic views for explaining a method for producing a microchannel. FIG. 2 is a flowchart representing the method for producing a microchannel. Each step in the production method will be explained with reference to FIG. 1(A) to FIG. 2.

First, as illustrated in FIG. 1(A), a substrate 1 is prepared, and an uncured layer of a curable resin 2 is formed on the substrate 1 (S1). Since the curable resin 2 in an uncured state has flowability, a frame (not illustrated) surrounding a perimeter is prepared, and the curable resin 2 is injected into the frame. As the curable resin 2, for example, an ultraviolet cured resin such as an acrylic resin or an epoxy resin is used. Alternatively, the curable resin 2 may be a thermosetting resin such as a urea resin, a melamine resin, or a phenolic resin. When a microchannel with a diameter of around several-hundred μm is formed, the thickness d of the curable resin 2 may be around 1000 μm.

Subsequently, a needle (needle body) 3 that can inject a liquid is inserted into the curable resin 2 (S2). The needle 3 has a hollow shape tapering down toward a tip thereof, such as the shape of an injection needle, and includes an opening (not illustrated) in the tip. In this case, a depth to which the needle 3 is inserted is set at, for example, around half of the thickness d of the curable resin 2. Alternatively, a needle in which the opening is disposed on a side in the vicinity of a tip of the needle may be used.

Then, a liquid 4 is injected in a tubular shape into the curable resin 2 via the needle 3 while moving the needle 3 (S3), as illustrated in FIG. 1(B). For example, in order to form a channel with a straight line shape, the needle 3 is moved in parallel along an X direction illustrated in FIG. 1(B). In addition, the liquid 4 is injected from the opening in the tip of the needle 3 into the layer of the curable resin 2 by pressurization from the upper portion of the needle 3 while moving the needle 3. In the layer of the curable resin 2, the liquid 4 has an approximately circular cross section perpendicular to the X direction due to surface tension.

Examples of the liquid 4 include liquid crystal. As used herein, "liquid crystal" is a substance that has flowability such as the flowability of a liquid and includes regular molecular orientation such as the molecular orientation of crystals. In addition, as the liquid 4, a liquid may also be used depending on the application of the formed channel. However, the injected liquid 4 may rise to a surface of the resin layer depending on the viscosity of the curable resin 2 or on a difference between the densities of the curable resin 2 and the liquid 4. Therefore, it is necessary to select, as the liquid 4, a liquid that can be injected in a tubular shape into the curable resin 2 depending on the relationship between the viscosity and the density.

After the injection of the liquid 4, the needle 3 is extracted from the curable resin 2 (S4). In this case, the curable resin 2 is not yet cured, and therefore, a hole opened in the curable resin 2 by the needle 3 is closed by extracting the needle 3. As a result, the liquid 4 is confined within the curable resin 2 and placed in the tubular shape.

As illustrated in FIG. 1(C), the curable resin 2 is cured to confine the liquid 4 within the curable resin 2 to thereby form a portion, in which the liquid 4 is present, as a channel 4A for a liquid (S5). When an ultraviolet cured resin is used as the curable resin 2, the curable resin 2 is cured by irradiation with ultraviolet rays. When a thermosetting resin is used as the curable resin 2, the curable resin 2 is cured by heating. As a result, the channel 4A with an approximately circular cross section is formed in a tubular region injected with the liquid 4.

Depending on the kind of the liquid 4, the liquid 4 may penetrate through the resin layer and the channel 4A may become hollow when the curable resin 2 is cured. A part of the cured curable resin may be removed to extract the liquid 4 confined within the curable resin 2, if a hollow channel is needed when the liquid 4 remains in the channel 4A even after curing the curable resin 2. An as a result, the hollow channel is obtained.

According to the present production method explained above, a channel with an approximately circular cross section is formed without affixing channels with semicircular cross sections to each other. Therefore, in the present production method, a circular channel that does not have any joined surface but has a smooth inner wall can be formed in fewer steps than those of a conventional production method that does not include the present configuration. In addition, the closed channel without any inlet can be formed since any opening is not present when the channel is formed.

As described above, the liquid 4 injected into the layer of the curable resin 2 has an approximately circular cross section perpendicular to the direction of extension of the liquid 4 due to surface tension. As a result, the cross section of the finally obtained channel has an approximately circular shape with neither depression nor sharp portion. The term "approximately circular shape" mentioned above refers to a shape without any sharp protruding portion, as included in a rectangular shape, in which the rate of a difference between maximum and minimum diameters to the maximum diameter is, for example, 10% or less.

In a bio-related system such as a biosensor or μTAS (Total Analysis System), a circular channel having a structure similar to an actual biological structure is preferred for more accurately reproducing a behavior in an in vivo structure such as, for example, a blood vessel. The channel obtained in the present production method can also be utilized in such a bio-related system.

When a channel filled with a liquid is needed, it is necessary to inject the liquid into a hollow channel after the channel is formed, in a production method that does not include the present configuration. In contrast, formation of a channel and filling of a liquid are performed in one step since the channel including the liquid therein is formed in the present production method. Therefore, in the present production method, a channel filled with a liquid can be formed in fewer steps than those of a production method that does not include the present configuration.

Additionally, by allowing the liquid confined within the channel to flow out, a hollow channel can be formed, and another liquid can also be injected after allowing the liquid to flow out. Therefore, an optional liquid can be filled into the formed channel regardless of the viscosity of the curable resin 2 and of a difference between the densities of the curable resin 2 and the liquid 4.

EXAMPLES

An experiment for forming a channel was conducted by the production method of FIG. 2 using acrylic resins as curable resins and using, as liquids to be injected, MLC-7018 and MDA-003461 which were P-type liquid crystals manufactured by Merck. FIG. 3(A) and FIG. 3(B) are photographs representing the experimental results of the production method of FIG. 2. FIG. 3(A) is a photograph for viewing, from above, the acrylic resins 12 injected (dispensed) with the two P-type liquid crystals 14 described above, respectively. FIG. 3(B) is a photograph of a cross section of a channel 4A, taken after curing the acrylic resins 12 by irradiation with ultraviolet rays. In this experiment, each P-type liquid crystal 14 was dispensed in the form of two straight lines parallel to each other into each acrylic resin 12.

Figure 4:
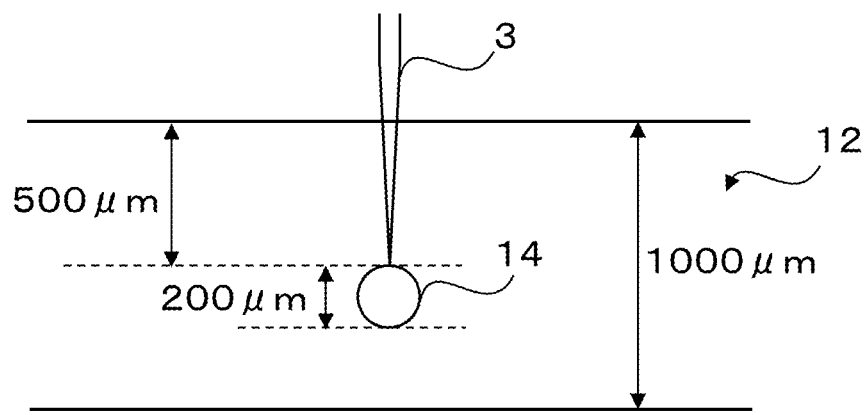
FIG. 4 is a schematic view for explaining the formation location and size of the formed channel illustrated in FIG. 3(B).

FIG. 4 is a schematic view for explaining the formation location and size of the formed channel 4A illustrated in FIG. 3(B). In the experiment described above, each acrylic resin 12 was formed in a layer shape with a thickness of 1000 μm, and a needle 3 was inserted to a depth of 500 μm in each acrylic resin 12. In addition, a dispensing pressure of 10 kPa was applied while moving the needle 3 at a speed of 20 mm/sec in straight line form along the surface direction of each acrylic resin 12, and each P-type liquid crystal 14 was dispensed so as to have a circular cross section with a diameter of 200 μm.

The channel 4A having the cross section as illustrated in FIG. 3(B) was obtained by extracting the needle 3 and then curing each acrylic resin 12 with ultraviolet rays. FIG. 3(B) also illustrates the outline of the cross section of the channel 4A together. The difference between the maximum and minimum diameters of the cross section is around 20 μm, and the rate of the difference between the maximum and minimum diameters to the maximum diameter of the cross section is within around several percent. As described above, it has been confirmed that a channel 4A with an approximately circular cross section is formed by the present production method.

REFERENCE SIGNS LIST

1 substrate
2 curable resin
3 needle
4 liquid
4A channel

What is claimed is:

1. A method for producing a microchannel, comprising the steps of:
    forming a layer of an uncured curable resin on a substrate;
    inserting into the curable resin a needle body that can inject a liquid;
    injecting a liquid in a tubular shape into the curable resin via the needle body while moving the needle body;
    extracting the needle body from the curable resin; and
    curing the curable resin to form a channel in a tubular region injected with the liquid.

2. The method according to claim 1, wherein the channel is a channel comprising an approximately circular cross section without any joined surfaces.

3. The method according to claim 1, further comprising the step of removing a part of the cured curable resin to extract the liquid confined within the curable resin.

4. The method according to claim 1, wherein the liquid is a liquid crystal.

\* \* \* \* \*